US010294483B2

(12) United States Patent
Lillehoj et al.

(10) Patent No.: US 10,294,483 B2
(45) Date of Patent: May 21, 2019

(54) ***EIMERIA TENELLA* ELONGATION FACTOR-1 ALPHA RECOMBINANT IMMUNOGENIC COMPOSITIONS WHICH INDUCE ACTIVE PROTECTIVE IMMUNITY AGAINST AVIAN COCCIDIOSIS**

(71) Applicant: The United States of America, as represented by the Secretary of Agriculture, Washington, DC (US)

(72) Inventors: Hyun S. Lillehoj, West Friendship, MD (US); Sungtaek Oh, Ellicott City, MD (US); Alfredo Panebra, Chevy Chase, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 15/887,130

(22) Filed: Feb. 2, 2018

(65) Prior Publication Data

US 2018/0230475 A1 Aug. 16, 2018

Related U.S. Application Data

(60) Provisional application No. 62/458,101, filed on Feb. 13, 2017.

(51) Int. Cl.

| | |
|---|---|
| *C07K 14/44* | (2006.01) |
| *A61K 39/002* | (2006.01) |
| *C12N 15/70* | (2006.01) |
| *A61P 33/02* | (2006.01) |
| *A61K 39/012* | (2006.01) |
| *C07K 14/455* | (2006.01) |
| *A61K 39/00* | (2006.01) |

(52) U.S. Cl.

CPC ............ *C12N 15/70* (2013.01); *A61K 39/012* (2013.01); *A61P 33/02* (2018.01); *C07K 14/44* (2013.01); *C07K 14/455* (2013.01); *A61K 2039/522* (2013.01); *A61K 2039/552* (2013.01)

(58) Field of Classification Search

None

See application file for complete search history.

(56) References Cited

U.S. PATENT DOCUMENTS

| | | | |
|---|---|---|---|
| 9,889,196 | B2 | 2/2018 | Ben Arous et al. |
| 2016/0256544 | A1 | 9/2016 | Ben Arous et al. |

FOREIGN PATENT DOCUMENTS

| | | |
|---|---|---|
| KR | 1020050076419 A | 7/2005 |

OTHER PUBLICATIONS

Holmes, 2001 Exp. Opin.Invest. Drugs, 2001, 10(3):511-519.*
Greenspan et al 1999, Nature Biotechnology, 7:936-937.*
Houghten et al. 1986 (Vaccines, Edited by Fred Brown: Cold Spring Harbor Laboratory) pp. 21-25.*
NCBI, GenPept accession No. XP_013234784.1, Elongation factor 1-alpha, related [Eimeria tenella], (2016), pp. 1-2.
Matsubayashi, Makoto et al., Elongation Factor-1 Is a Novel Protein Associated with Host Cell Invasion and a Potential Protective Antigen of Cryptosporidium parvum*, Journal of Biological Chemistry, (2013), 288(47): 34111-34121.
Reid, Adam J., Genomic analysis of the causative agents of coccidiosis in domestic chickens, Genome Research Published by Cold Spring Harbor Laboratory Press, (2018), 24:1676-1685.
Lin, Rui-Qing, Vaccination with Eimeria tenella elongation factor-1α recombinant protein induces protective immunity against E. tenella and E. maxima infections, Veterinary Parasitology, (2017), 243:79-84.
Seoul National University Industry Foundation and Avicore Bio Technology Institute, Inc., Recombinant SCFV Antibodies Specifice to Surface Antigen from Sporozoite of *Eimeria* SPP. Responsible for Coccidiosis Which Have Enhanced Specificity to Surface Antigen from Sporozoite of *Eimeria* SPP., (2005).
International Searching Authority, PCT/US2018/017006 for The United States of America, as Represented by the Secretary of Agriculture et al., International Filing Date Feb. 6, 2018.

* cited by examiner

*Primary Examiner* — Padmavathi Baskar

(74) *Attorney, Agent, or Firm* — John D. Fado; Mark D. McNemar

(57) ABSTRACT

Provided herein are immunogenic compositions containing recombinant proteins capable of presenting all, or antigenic portions of, the *Eimeria tenella* Elongation Factor 1 alpha, or EF-1α, protein in the development of active immunity to, and control of, coccidiosis. Also provided are methodologies of using the immunogenic compositions for administration to poultry and other animals in the control of coccidiosis. In some instances, the EF-1α protein utilized in the immunogenic composition presented herein is molecularly manipulated or combined with adjuvants to increase effectiveness.

14 Claims, 6 Drawing Sheets

Specification includes a Sequence Listing.

EIMERIA TENELLA ELONGATION FACTOR-1 ALPHA RECOMBINANT IMMUNOGENIC COMPOSITIONS disclosure provides an immunogenic composition, comprising an isolated *Eimeria tenella* EF-1α protein (SEQ ID NO: 2), an isolated protein having at least 95% homology to *Eimeria tenella* EF-1α (SEQ ID NO: 2), or an isolated protein comprising an antigenic portion of *Eimeria tenella* EF-1α (SEQ ID NO: 2), and a pharmaceutically or veterinarily acceptable carrier wherein the immunogenic composition is capable of inducing an immune response to said isolated protein in a recipient. In some embodiments, the immunogenic compositions disclosed herein comprise an adjuvant, such as ISA 71. In other embodiments, the isolated *Eimeria tenella* EF-1α protein is expressed by a recombinant host cell comprising an exogenous nucleic acid encoding the isolated protein, such as a recombinant *Escherichia coli* cell. In some embodiments, the carrier is a liquid carrier. Immunogenic compositions of the present invention can be formulated for parenteral, intramuscular, or oral delivery.

Also provided herein is a method of protecting a recipient against coccidiosis, comprising administering to the recipient an immunogenic composition comprising an isolated *Eimeria tenella* EF-1α protein (SEQ ID NO: 2), an isolated protein having at least 95% homology to *Eimeria tenella* EF-1α (SEQ ID NO: 2), or an isolated protein comprising an antigenic portion of *Eimeria tenella* EF-1α (SEQ ID NO: 2) in an amount effective to induce a protective immune response to an *Eimeria* species. In practicing such methodologies, an adjuvant can also be administered to the recipient. In some embodiments, the protective immune response is to *E. tenella*, *E. maxima*, or *E. acervulina*. In particular embodiments, the recipient is a poultry species, such as chickens or turkeys. In other embodiments, the immunogenic composition is administered to the recipient at a dose of at least 50 μg of recombinant *Eimeria tenella* EF-1α. In still other embodiments, immunogenic compositions of the present invention are administered parenterally, intramuscularly or orally.

Further provided herein are immunogenic compositions produced by the steps of: 1) culturing a recombinant host cell transformed with a gene encoding *Eimeria tenella* EF-1α (e.g., SEQ ID NO: 1), a DNA sequence encoding a protein having at least 95% homology to *Eimeria tenella* EF-1α (as compared to SEQ ID NO: 2), or a DNA sequence encoding a protein comprising an antigenic portion of *Eimeria tenella* EF-1α (SEQ ID NO:2); 2) expressing the protein encoded by the recombinant DNA; 3) purifying the protein produced; and 4) incorporating the purified protein in or on a pharmacologically or veterinarily acceptable carrier. In some embodiments, an adjuvant such as ISA 71 is also incorporated. In still other embodiments, the host cell expressing the protein is a bacterial cell, such as an *Escherichia coli* cell.

Incorporation by Reference

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

FIGS. 4A and 4B provide graphs showing the effects of vaccination with recombinant EF-1α protein on body weight gain from Trial 1 and Trial 2.

FIGS. 5A and 5B provide graphs showing the effects of vaccination with recombinant EF1α protein on fecal oocyst shedding from Trial 1.

FIGS. 6A and 6B provide graphs showing the effects of vaccination with recombinant EF-1α on serum IgG antibody levels during experimental avian coccidiosis.

DETAILED DESCRIPTION OF THE INVENTION

As described herein, the EF-1α genomic sequence was amplified from *E. tenella* DNA, and found to contain one intron. After removing the intron, the *E. tenella* EF-1α coding sequence was cloned into the pET32α(+) plasmid vector and confirmed by sequencing. The recombinant EF-1α protein was detected by SDS-PAGE and Western blot as expected. Then the immune protection it induced in chicken was evaluated and $1 \times 10^4$ sporulated oocysts of *E. tenella*, *E. acervulina* or *E. maxima* were used for challenging infections. In general, chickens immunized with rEF-1α showed increased weight gains and reduced fecal oocyst shedding compared with non-vaccinated controls. When vaccinated only with EF-1α, antigen-specific humoral antibodies were not found to be increased, however, the results showed ISA 71 adjuvant could significantly increase the IgG level against EF-1α. The effect of ISA 71 adjuvant on enhancing immunization has also been demonstrated in other similar reports (Jang et al., supra; Jang et al., PLoS One (2013) 8:e59786).

Presented herein are evaluations of the immunization effects of rEF-1α against *E. tenella*, or *E. maxima* challenge by measuring body weight gain, fecal oocyst shedding and antibody response. These result revealed rEF-1α can induce a protective effect against different *Eimeria* species, suggesting that EF-1α should provide a promising immunogenic composition candidate against *Eimeria* infection.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The term "about" is defined as plus or minus ten percent of a recited value. For example, about 1.0 g means 0.9 g to 1.1 g and all values within that range, whether specifically stated or not.

The term a nucleic acid or protein "consisting essentially of", and grammatical variations thereof, means: 1) nucleic acids that differ from a reference sequence by 20 or fewer nucleic acid residues and also perform the function of the reference nucleic acid sequence, and 2) proteins that differ from a reference sequence by 10 or fewer nucleic acids and also perform the function of the reference protein sequence. Such variants include sequences which are shorter or longer than the reference sequence, have different residues or amino acids at particular positions, or a combination thereof.

The term "comprising" as used herein will be understood to mean that the list following is non-exhaustive and may or may not include any other additional suitable items, for example one or more further feature(s), component(s) and/or ingredient(s) as appropriate.

The terms "EF-1α" and "Elongation Factor 1 alpha" are synonyms and refer to the protein defined herein as SEQ ID NO: 2 and encoded by the DNA of SEQ ID NO: 1 (or any version of SEQ ID NO: 1 with base substitutions that result in a protein with a sequence identical to SEQ ID NO: 2). These terms also refer to modified versions of these SEQ ID NOs, such as those comprising regulatory nucleic acids, or proteins (and the nucleic acids encoding them) containing additional moieties allowing for purification or immunogenicity-enhancement. Where indicated, these terms can also include antigenic sub-portions of the provided protein sequence(s).

As used herein, the term "poultry" refers to one bird, or a group of birds, of any type of domesticated birds typically kept for egg and/or meat production. For example, poultry includes chickens, ducks, turkeys, geese, bantams, quail, pheasant, pigeons, or the like, preferably commercially important poultry such as chickens, ducks, geese and turkeys.

The terms "isolated", "purified", or "biologically pure" as used herein, refer to material that is substantially, or essentially, free from components that normally accompany the referenced material in its native state.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

In practicing some embodiments of the invention disclosed herein, it can be useful to modify the genomic DNA of a recombinant strain of a host cell producing the immunogenic protein of the immunogenic compositions (e.g., EF-1α protein). In preferred embodiments, such a host cell is E. coli. Such modification can involve deletion of all or a portion of a target gene, including but not limited to the open reading frame of a target locus, transcriptional regulators such as promoters of a target locus, and any other regulatory nucleic acid sequences positioned 5' or 3' from the open reading frame. Such deletional mutations can be achieved using any technique known to those of skill in the art. Mutational, insertional, and deletional variants of the disclosed nucleotide sequences and genes can be readily prepared by methods which are well known to those skilled in the art. It is well within the skill of a person trained in this art to make mutational, insertional, and deletional mutations which are equivalent in function to the specific ones disclosed herein.

Where a recombinant nucleic acid is intended for expression, cloning, or replication of a particular sequence, DNA constructs prepared for introduction into a prokaryotic or eukaryotic host will typically comprise a replication system (i.e. vector) recognized by the host, including the intended DNA fragment encoding a desired polypeptide, and can also include transcription and translational initiation regulatory sequences operably linked to the polypeptide-encoding segment. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) *Current Protocols in Molecular Biology*, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Preferred host cells are members of the genus *Escherichia*, especially *E. coli*. However, any suitable bacterial, protist, animal or fungal host capable of expressing the described proteins can be utilized. Even more preferably, non-pathogenic and non-toxigenic strains of such host cells are utilized in practicing embodiments of the disclosed inventions. Examples of workable combinations of cell lines and expression vectors are described in Sambrook et al. (1989); Ausubel et al. (Eds.) (1995) *Current Protocols in Molecular Biology*, Greene Publishing and Wiley Interscience, New York; and Metzger et al. (1988) *Nature,* 334: 31-36. Recombinant host cells, in the present context, are those which have been genetically modified to contain an isolated nucleic molecule, or produce a recombinant protein, of the instant invention. The nucleic acid(s) encoding the protein(s) of the present invention can be introduced by any means known to the art which is appropriate for the particular type of cell, including without limitation, transformation, lipofection, electroporation or any other methodology known by those skilled in the art.

Immunogenic Compositions

An immunogenic composition is defined herein as a biological agent which is capable of providing a protective response in an animal to which the immunogenic composition has been delivered and is incapable of causing severe disease. Administration of the immunogenic compositions result in increased immunity to a disease; the immunogenic compositions stimulate antibody production, cellular immunity, or both against the pathogen causing the disease. Immunity is defined herein as the induction of a significantly higher level of protection in a population of recipients, such as poultry, against mortality and clinical symptoms after receipt of an immunogenic composition compared to an untreated group. In particular, the immunogenic composition(s) according to the invention can: (a) protect a large proportion of treated animals against the occurrence of clinical symptoms of the disease and mortality, or; (b) result in a significant decrease in clinical symptoms of the disease and mortality.

The immunogenic composition(s) of the invention herein, regardless of other components included, comprise a recombinant EF-1α protein from *E. tenella*. EF-1α proteins of the present invention can comprise the entirety of SEQ ID NO: 2, or antigenic portions thereof. EF-1α proteins of the present invention can also include those with 90%, 91%, 92%, 93%, 94%, 95%, 96%, 97%, 98%, 99%, or higher homology to the protein of SEQ ID NO: 2.

The immunogenically effective amounts of immunogenic compositions disclosed herein can vary based upon multiple parameters. In general, however, effective amounts per dosage unit can be about 10-200 μg recombinant EF-1α protein, about 20-150 μg recombinant EF-1α protein, or about 50-100 μg recombinant EF-1α protein. An individual dose can contain 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more μg of recombinant EF-1α protein per dose. These amounts can also include antigenic portions of the full length EF-1α protein.

One, two, or more dosage units can be utilized in practicing the methodologies of the present invention. If two dosage units are selected, then vaccination at about day 1 post-hatch and again at about one week to two weeks of age is preferred. A dosage unit can readily be modified to fit a desired volume or mass by one of skill in the art. Regardless of the dosage unit parameters, immunogenic compositions disclosed herein can be administered in an amount effective to produce an immune response to the presented antigen (e.g., EF-1α protein). An "immunogenic ally effective amount" or "effective amount" of an immunogenic composition as used herein, is an amount of the composition that provides sufficient levels of antigenic protein to produce a desired result, such as induction of, or increase in, production of antibody specific to the antigen, protection against coccidiosis, as evidenced by a reduction in gastrointestinal lesions, increased weight gain, and decreased oocyst shedding and other indicators of reduction in pathogenesis. Amounts of immunogenic compositions capable of inducing such effects are referred to as an effective amount, or immunogenically effective amount, of the immunogenic compositions.

Dosage levels of active ingredients (e.g., EF-1α protein) in immunogenic compositions disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. As used herein, the term "minimal dose" or "minimal effective dose" refers to a dose that demonstrates the absence of, or minimal presence of, toxicity to the recipient, but still results in producing a desired result (e.g., protective immunity). Minimal effective doses, or minimum immunizing doses, of the recombinant immunogenic compositions provided herein can include about 10-200 μg recombinant EF-1α protein, about 20-150 μm recombinant EF-1α protein, or about 50-100 μm recombinant EF-1α protein. The minimal effective doses can also be any dose within the range of 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more μg of recombinant EF-1α protein per dose. These amounts can also include antigenic portions of the full length EF-1α protein. Determination of a minimal dose is well within the capabilities of one skilled in the art.

Formulations

In some instances, immunogenic compositions of the present invention also contain or comprise one or more adjuvants, which includes any material included in the immunogenic composition formulation that enhances an immune response in the recipient that is induced by the immunogenic composition. In some instances, such adjuvants can include proteins other components included with the antigenic protein (e.g., EF-1α protein). Non-limiting examples of such adjuvants can include engineered proteins in which the (e.g., EF-1α protein) is expressed as a fusion protein operably linked with immunity-enhancing moieties. Other adjuvants can be included as an extra component of the immunogenic compositions, and include such categories as aluminum salts (alum), oil emulsions, saponins, immune-stimulating complexes (ISCOMs), liposomes, microparticles, nonionic block copolymers, derivatized polysaccharides, cytokines, and a wide variety of bacterial derivatives. Such adjuvants can include, for example, ISA 71, IMS 1313, immunostimulating complex, AB5 toxins (e.g., cholera toxin), *E. coli* heat labile toxin, monophosphoryl lipid A, flagellin, c-di-GMP, inflammatory cytokines, chemokines, definsins, chitosan, phytochemicals, and combinations of these. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present invention can also comprise pharmaceutically or veterinarily acceptable carriers in addition to the recombinant protein component. Carriers utilized in practicing the immunogenic compositions provided herein can be any known in the art and can be liquid, solid, semi-solid, or gel. The type of formulation can be modified depending on the route of administration of the antigen. For example, if the immunogenic compositions of the present invention are applied parenterally (intramuscularly, intravascularly, or subcutaneously), a liquid formulation—such as an emulsion, suspension, or solution—is preferred. For oral administration, the immunogenic compositions of the present invention can be applied to carriers such as pellets, tablets, kibbles, chewables, powders and beads, as well as specific materials such as microcrystalline cellulose (MCC), plant-based products and soil-based products (e.g., clays). Preferably, carriers are non-toxic to the recipient. In some instances the immunogenic compositions of the present invention, with or without carriers, can be presented to a recipient for ingestion via suspension in drinking water. One of skill in the art is readily able to choose such carriers for application to recipient animals such as poultry.

Administration Methodologies

The present disclosure provides compositions for introducing a recombinant immunogenic composition containing, at a minimum, a recombinant *E. tenella* EF-1α protein, or antigenic fragments thereof, into targets (e.g., poultry). Thus, the compositions provided herein can be utilized to induce immunity to *Eimeria* species (e.g., *E. tenella*) and more generally, the disease coccidiosis in targets to which the antigen is provided.

An immunogenic composition of the present invention can be administered intramuscularly, intradermally, subcutaneously, intranasally, by injection, or via ingestion in an amount which is effective to protect the recipient (e.g., poultry). Application of an immunogenic composition to a subject can result in the development of immunity to the EF-1α protein, preferably development of an effective immune response that results in the decrease or removal of clinical symptoms. Application of the immunogenic compositions of the present invention can be provided at multiple times or in a single dosage. Application of the immunogenic compositions provided herein to poultry can occur for the first time about day 1 post-hatch or any time thereafter. Application can be performed before, during or after the development of *Eimeria*-caused coccidiosis, including coccidiosis caused by *E. tenella*, *E. maxima*, *E. acervulina*, and other *Eimeria* species.

Having generally described this invention, the same will be better understood by reference to certain specific examples, which are included herein to further illustrate the invention and are not intended to limit the scope of the invention as defined by the claims.

EXAMPLES

Example 1

Experimental Design.

Figure 1:
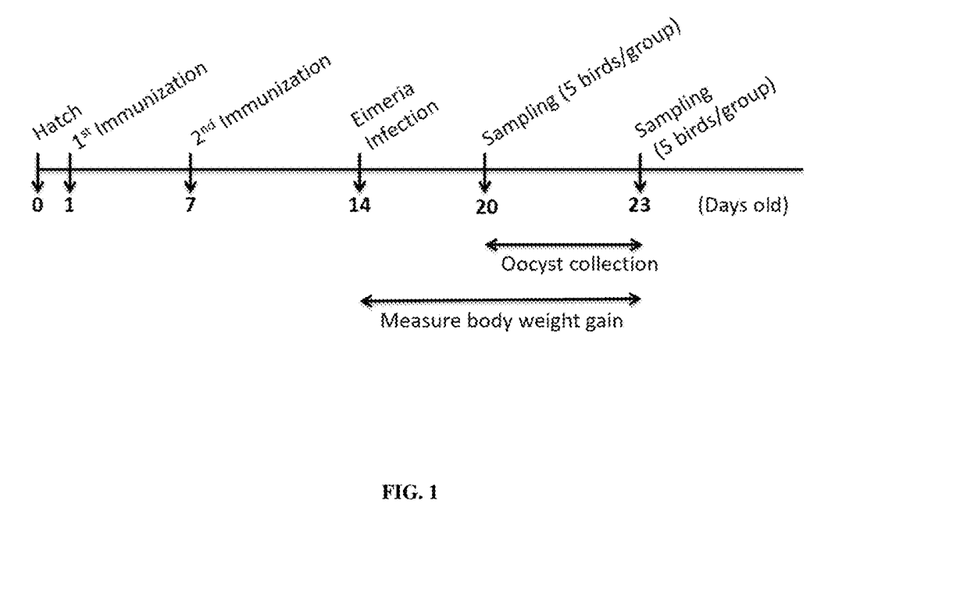
FIG. 1 provides a schematic outline of experimental designs detailed herein.

Two separate animal trials were carried out to evaluate the immunogenic composition efficacy of the EF1α protein against avian coccidiosis. The experimental design is illustrated in Table 1 and FIG. 1. At 1d of age, commercial broiler chickens (15 or 20/group) were subcutaneously immunized with 50 or 100 ug of rEF-1α. Control animals received PBS alone. At 1 week post-immunization, animals were given a booster injection with the same immunogenic compositions. At 7 d post-secondary immunization, chickens were given PBS or $1.0 \times 10^4$ *Eimeria* sp. sporulated oocysts by oral gavage using an 18-gauge needle. Chickens were immunized twice with PBS (Control), rEF-1α protein alone or with rEF-1α protein/ISA 71 at 1 and 7 days post-hatch subcutaneously, and infected with *Eimeria* sp. (*E. tenella* or *E. maxima*) at 7 days post-secondary immunization.

TABLE 1

Experimental groups vaccinated with rEF-1α protein

| Trial number | Group | Immunogen | Adjuvant | Number of Birds | Infection |
|---|---|---|---|---|---|
| Trial #1 | 1-1 | PBS (100 ul/bird) | — | 20 | — |
| | 1-2 | PBS (100 ul/bird) | — | 20 | *E. tenella* ($1 \times 10^4$/ml) |
| | 1-3 | EF1α (50 ug/bird) | — | 20 | *E. tenella* ($1 \times 10^4$/ml) |
| | 1-4 | EF1α (100 ug/bird) | — | 20 | *E. tenella* ($1 \times 10^4$/ml) |
| Trial #2 | 1-1 | PBS (100 ul/bird) | — | 15 | — |
| | 1-2 | PBS (100 ul/bird) | — | 15 | *E. maxima* ($1 \times 10^4$/ml) |
| | 1-3 | EF1α (100 ug/bird) | — | 15 | *E. maxima* ($1 \times 10^4$/ml) |

Experimental Animals

One day-old male broiler chickens (Ross strain, Longenecker's Hatchery, Elizabethtown, Pa.) were reared in floor pan cages and provided with feed and water ad libitum. At 14 days post-hatch, the chickens were transferred to hanging cages with two birds per cage. All procedures were approved by the Beltsville Area Institutional Animal Care and Use Committee.

Parasites

The strains of *E. tenella*, *E. maxima* and *E. acervulina* used in this study were originally developed and maintained at the Animal Biosciences and Biotechnology Laboratory of the Beltsville Agricultural Research Center (Beltsville, Md.). Oocysts were cleaned by flotation on 2.5% sodium hypochlorite, washed three times with PBS, and enumerated using a hemocytometer prior to experimental infections as described (Jang et al., 2010, supra).

Statistical Analysis

All data are expressed as means±S.D. values and subjected to one-way analysis of variance using SPSS software (SPSS 15.0 for windows, Chicago, Ill.). Duncan's multiple range test was used to analyze differences between the mean values. Differences were considered statistically significant at $P<0.05$.

Example 2

Cloning and Expression of Recombinant EF-1α Protein from *E. tenella*.

Figure 2:
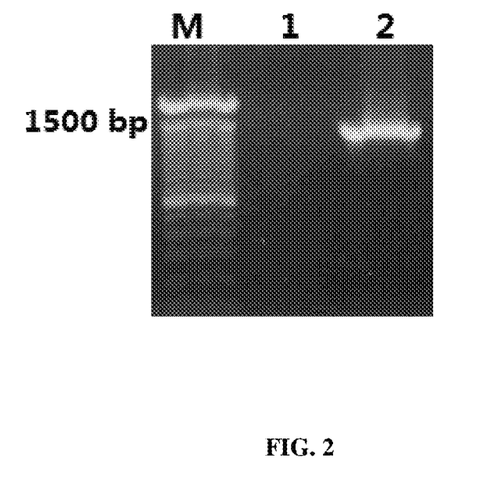
FIG. 2 provides an image of agarose gel electrophoresis of a PCR product of the EF-1α coding sequence from *E. tenella*.
Figure 3:
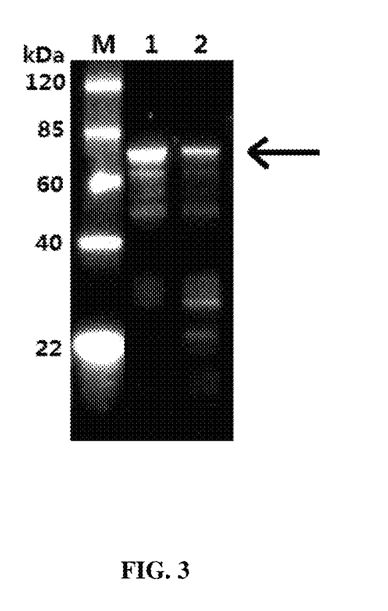
FIG. 3 provides an image of Western blot analysis of recombinant EF-1α protein. The lanes are as follows: M—Marker; Lane 1—supernatant of cell lysate with overnight induction at 15° C.; Lane 2—supernatant of cell lysate with 4 hour induction at 37° C.

The EF1α sequence (containing an intron) amplified by PCR from *E. tenella* DNA was ~1800 bp in length and consists of 450 amino acids (49,101.54 daltons) (data not shown). After removing the intron, the PCR product representing the coding sequence of EF1α (FIG. 2, ~1400 bp) was cloned into T vector (Invitrogen, USA), and then subcloned into pET32a (+) expression vector and sequenced. The nucleotide sequence (SEQ ID NO: 1) was identical to the published *E. tenella* EF-1α sequence (GenBank accession no. JN987661). The expression of recombinant proteins containing an His6 epitope tag (615 amino acids) with estimated molecular weight of 66,804.1 was detected by SDS-acrylamide gel and showed mainly in the inclusion body form. The protein expression was further confirmed by Western blotting using a monoclonal antibody (anti-His monoclonal-antibody (Genscript, Cat. No. A00186)) against the His epitope tag (FIG. 3).

Construction of the Prokaryotic Expression Plasmid pET-EF-1α

The purified oocysts of *E. tenella* were washed in phosphate buffered saline (PBS), disrupted in glass beads, and the total genomic DNA was extracted using the sodium dodecyl sulphate/proteinase K, followed by phenol/chloroform method. The purity of *E. tenella* was confirmed by specific PCR as previously described (Fernandez et al., Parasitol. (2003) 127:317-25). The sequence of *E. tenella* EF-1α gene (containing an intron) was amplified by PCR from genomic DNA of *E. tenella* with a pair of oligonucleotide primers (EF-1αF: 5'-TGCT<u>GGATCC</u>ATGGGGAAGGAAAAG-3' (SEQ ID NO: 3), and EF-1αR: 5'-CACA<u>AAGCTT</u>GTCACTTCTTGGCG-3' (SEQ ID NO: 4)), and BamH I and HindIII recognition sites were introduced (underlined sequences). The PCR product was cloned into T plasmid vector (TOPO® TA Cloning® Kit, Invitrogen, USA) and sequenced in both directions.

Subsequently, the intron was removed by amplifying and connecting two segments of EF-1α coding sequence with two pairs of primers respectively ((EF1αF/EF1αR2: GTTCCCGCGTCTGCCCTTCCTTGGAGA (SEQ ID NO: 5); EF1αF2: TCTCCAAGGAAGGGCAGACGCGGGAAC/EF1αR (SEQ ID NO: 6)) using PfuUltra II fusion HS DNA Polymerase (Agilent Technologies Inc., USA). The EF-1α PCR product (without intron) was cloned and sequenced to ensure fidelity. Then the coding sequence of EF-1α was cleaved using BamH I/HindIII from recombinant T ET-EF-1α plasmid expression vector and cloned into the pET32a(+) plasmid vector (Novagen/EMD Chemicals, Gibbstown, N.J.) downstream from an NH2-terminal His6 epitope tag. The recombinant plasmid clones of pET-EF1α were verified by sequence analysis.

Bacterial Expression and Purification of EF-1α Recombinant Protein

The recombinant plasmid pET-EF-1α was used to transform *E. coli* BL21(DE3), induced for 4 h with 1 mM IPTG at 37° C. and 15° C., and the cells harvested by centrifugation and sonication. The lysate was applied to Ni-NTA resin and Filter Column (HITrap®, GE Healthcare, Piscataway, N.J.), washed with PBS, Tris pH 7.4 and Tris pH 8.0 to remove unbound proteins, and bound proteins were eluted stepwise with PBS, pH 7.0 containing 0.25 M imidazole (Sigma). The eluted protein fractions were visualized on 12% sodium dodecyl sulfate polyacrylamide gel (SDS-PAGE) SDS-acrylamide gels stained with Coomassie brilliant blue and on Western blots probed with horseradish peroxidase-conjugated anti-His monoclonal antibody (Giagen), and stored at −20° C.

Example 3

Effect of EF-1α Vaccination on Body Weight Gain and Fecal Oocyst Shedding

Body weight gain and fecal oocyst shedding were used to evaluate the effect of EF1α immunization against *E. tenella*, or *E. maxima* challenge infection. Following challenge infection with *E. tenella* or *E. maxima*, the average body weight (FIGS. 4A and 4B) of chickens was higher and the fecal oocyst output (FIGS. 5A and 5B) were significantly decreased in all the vaccinated and challenged groups compared with non-vaccinated and challenged groups, indicating immunization with rEF-1α induced an effective, protective response.

Body Weight Gain

Figure 4A:
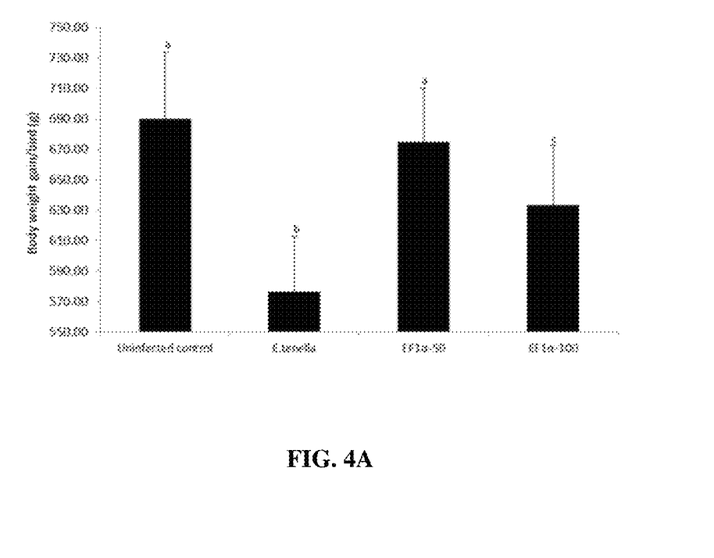
FIG. 4A shows results from experimental infection with *E. tenella*.
Figure 4B:
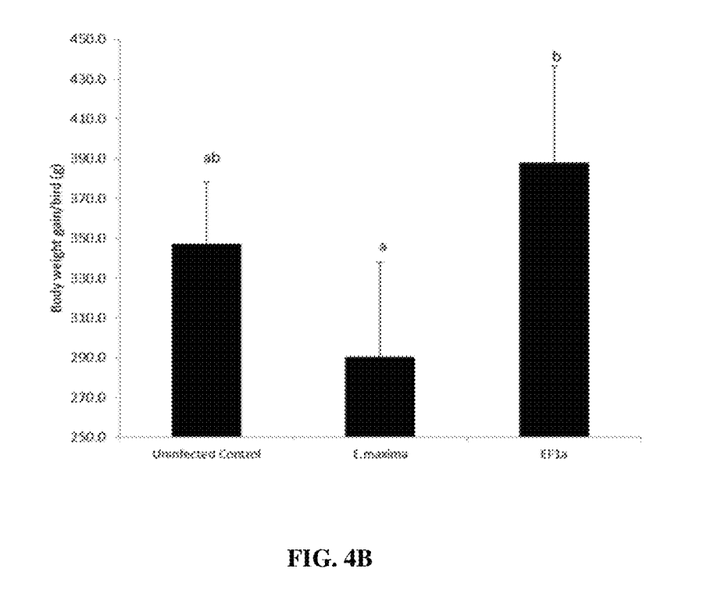
FIG. 4B shows results from experimental infection with *E. maxima*.

Uninfected and *Eimeria*-infected birds (8-12/group) were assessed for body weight changes between d0 to d6 for *E. tenella*, and d0 to d8 for *E. maxima* infection (23 day-old for *E. tenella* infection) post-infection. For Trial 1, chickens were infected with $1.0 \times 10^4$ sporulated *E. tenella* oocysts and body weight gains between 0 to 6 (FIG. 4A) days post-infection were determined. For Trial 2, chickens were infected with $1.0 \times 10^4$ sporulated *E. maxima* oocysts and body weight gains between 0 to 8 days (FIG. 4B) days post-infection were determined. In FIGS. 4A and 4B, each bar represents the mean±S.D. value (n=8–12) and within each graph, bars with different letters are significantly different according to the Duncan's multiple range test ($P<0.05$).

Oocyst Shedding

Figure 5A:
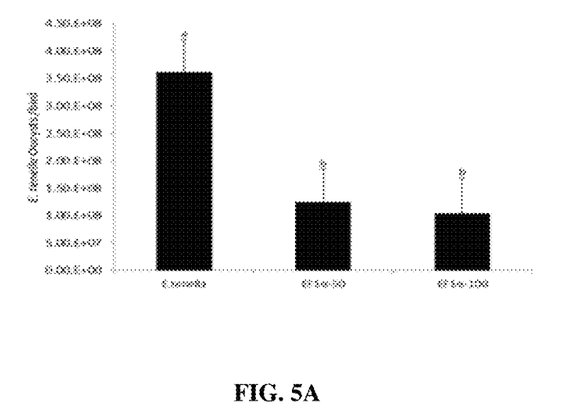
FIG. 5A shows results from experimental infection with *E. tenella*.
Figure 5B:
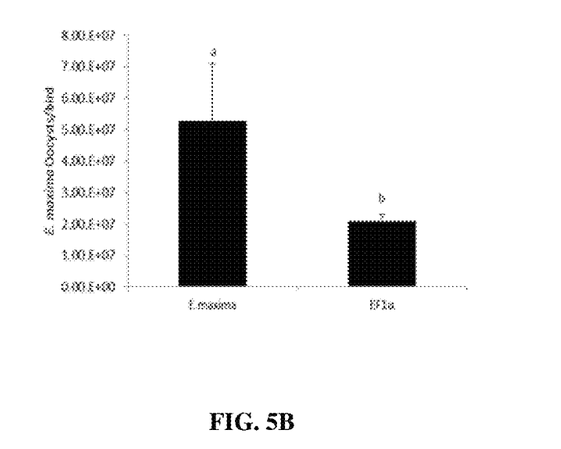
FIG. 5B shows results from experimental infection with *E. maxima*.

Fecal samples were collected from infected birds between 6 and 9 days (for *E. tenella*; FIG. 5A), or between 6 and 8 (for *E. maxima*; FIG. 5B) post-infection and oocysts were enumerated using a McMaster counting chamber as described (Ding et al., Infect. Immun. (2004) 72:6939-44). Two independent people counted oocysts.

For Trial 1, chickens were immunized with PBS (control), or rEF-1α protein. At 7 days post-immunization, the chickens were uninfected or infected with $1.0 \times 10^4$ sporulated *E. tenella* (FIG. 5A) oocysts and shedding between 6 to 9 days post-infection were determined. For Trial 2, chickens were immunized with PBS (control), or EF1α protein. At 7 days post-immunization, the chickens were uninfected or infected with $1.0 \times 10^4$ sporulated *E. maxima* (FIG. 5B) oocysts and shedding between 6 to 8 days post-infection was determined. In FIGS. 5A and 5B, each bar represents the mean±S.D. value (n=8) and within each graph, bars with different letters are significantly different according to the Duncan's multiple range test ($P<0.05$). Uninfected control animals did not exhibit any oocyst shedding (data not shown).

Example 4

Effect of EF-1α Vaccination on Humoral Antibody Response

In Trial 1 (FIG. 6A), chickens were subcutaneously immunized twice with 50 or 100 ug of EF1α. At 7 days post-secondary immunization, the animals were uninfected or infected with $1.0 \times 10^4$ *E. tenella* parasites. For Trial 2 (FIG. 6B), chickens were subcutaneously immunized twice with 100 ug of rEF-1α. At 7 days post-secondary immunization, the animals were uninfected or infected with $1.0 \times 10^4$ *E. maxima* parasites. Serum IgG antibody levels were measured by ELISA at 9 days post-infection for Trial 1 and 8 days post-infection for Trial 2.

Serum IgG antibody levels against rEF-1α protein were measured by an indirect enzyme-linked immunosorbent assay (ELISA) as described (Lee et al., Res. Vet. Sci. (2013) 95:110-14). Ninety-six well microtiter plates were coated overnight with 1.0 ug/well of purified recombinant EF-1α proteins which were expressed in *Escherichia coli*. The plates were washed with PBS containing 0.05% Tween 20 (PBS-T) and blocked with PBS containing 1% bovine serum albumin. Serum samples were diluted 1:50, 100 ul was added to each well, incubated with agitation for 1 h at room temperature, and washed with PBS-T. Bound antibodies were detected with peroxidase-conjugated rabbit anti-chicken IgG secondary antibody and tetramethylbenzidine substrate (Sigma, St. Louis, Mo.). Optical densities (OD) were measured using a microplate spectrophotometer (ELx800™, BioTek, Winooski, Vt.).

Figure 6A:
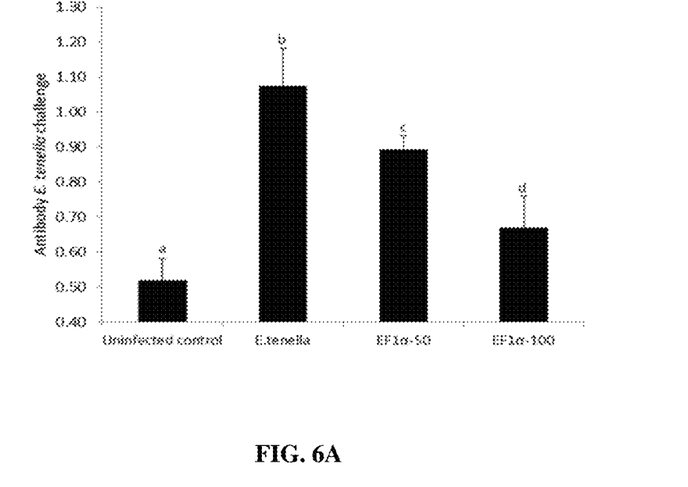
FIG. 6A shows results from experimental infection with *E. tenella*.
Figure 6B:
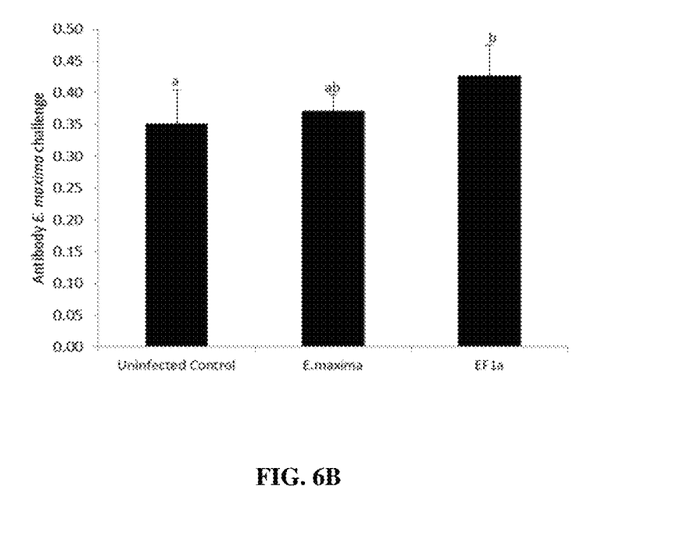
FIG. 6B shows results from experimental infection with *E. maxima*.

Results are shown in FIGS. 6A and 6B. Antibody levels are expressed as $\Delta$OD values ($OD_{450}$ vaccinated and infected group $-OD_{450}$ non-vaccinated, uninfected controls). Each sample was analyzed in triplicate and each bar represents the mean±S.D. value (n=5). Bars with different letters are significantly different according to the Duncan's multiple range test ($P<0.05$).

The data shows that compared with uninfected control and infected control, no higher antibody titers were detected at 9 days post-infection (for *E. tenella* infection; FIG. 6A) or at 8 days post-infection (for *E. maxima* infection; FIG. 6B) days post-vaccinated only with rEF-1α.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. An immunogenic composition, comprising a pharmaceutically or veterinarily acceptable carrier and a recombinant protein of SEQ ID NO: 2, wherein said immunogenic composition is capable of inducing an immune response to said protein in a recipient.

2. The immunogenic composition of claim 1, further comprising an adjuvant.

3. The immunogenic composition of claim 1, wherein the protein is expressed by a recombinant host cell comprising an exogenous nucleic acid encoding the protein.

4. The immunogenic composition of claim 3, wherein the host cell is an *Escherichia coli* cell.

5. The immunogenic composition of claim 1, wherein the carrier is a liquid carrier.

6. The immunogenic composition of claim 1, wherein the composition is formulated for parenteral delivery.

7. The immunogenic composition of claim 1, wherein the composition is formulated for oral delivery.

8. The immunogenic composition of any of claims 1-7, wherein the protein is an isolated protein.

9. A method of protecting a recipient against coccidiosis, comprising administering to the recipient an immunogenic composition according to claim 1 or claim 2 in an amount effective to induce a protective immune response to an *Eimeria* species.

10. The method of claim 9, wherein the recipient is a chicken or turkey.

11. The method of claim 9, wherein the immunogenic composition is administered to the recipient at a live whole-cell formulation at a dose of at least 50μg.

12. The method of claim 9, wherein the composition is administered parenterally.

13. The method of claim 12, wherein the composition is administered intramuscularly.

14. The method of claim 9, wherein the composition is administered orally.

* * * * *

SEQUENCE LISTING

<160> NUMBER OF SEQ ID NOS: 6

<210> SEQ ID NO 1
<211> LENGTH: 1354

```
<212> TYPE: DNA
<213> ORGANISM: Eimeria tenella

<400> SEQUENCE: 1 catgggaag gaaaagacgc acataaacct ggtggtgatc ggccacgtgg acagcgggaa     60
aagcaccacc acgggccacc tgatctacaa actcggcggc atcgacaaaa ggaccatcga    120
aaagttcgaa aaagagtctt ccgaaatggg caaggcctcc ttcaagtacg cctgggtcct    180
cgacaagctc aaggccgagc gcgagcgcgg catcaccatc gacatcgctc tctggcagtt    240
cgagactccc gccttccact acaccgtcat tgacgcgccg gccaccgcg  acttcatcaa    300 aaacatgatt accggcacgt ctcaggcgga cgtcgcgttg ctcgtcgtgc ctgcggacca    360
gggcggcttc gagggcgcct tctccaagga agggcagacg cgggaacacg cgctgctggc    420
gttcacgctg ggcgtgaagc agatgatcgt ggggataaac aaaatggacg cgacttcgcc    480
ggagaagtac agcgaggcgc ggttcaacga atccaagcc gaagtgtcgc ggtacctgaa     540
gacagtgggc tacaacccgg agaaagtgcc gttcgtgccg atctcaggct cgtgggcga     600 caacatggtg gagcgcagca gcaacatggg ctggtacaag gcaaaacgc  tggtggaggc    660 tttggacagc gtggagcccc cgaagcgccc cgtggacaag ccgctgcggc tgccgctgca    720
ggacgtgtac aagatcggcg ggatcggcac ggtccccgtg gggcgcgtgg agacgggcgt    780
gctgaagcca ggcatggtgg tgaccttcgc gccctcgggg ctgcagacgg aggtcaagtc    840
cgtggagatg caccacgcgc agctggagca ggccgtcccc ggagacaacg tgggcttcaa    900
cgtgaaaaac gtctccgtca aggacgtcaa gcgcggccac gtcgcctccg actccaagaa    960
cgaccccgcc aaggccgccg ccagcttcca ggcccaggtc atcgtcctgc accaccccgg   1020
ccagatcaac cccggctaca cgcccgtcct cgactgccac actgcgcaca tcagttgcaa   1080
gttcgccgac ctcgagaagc gcctcgaccg ccgcagcggc aaggctctcg aggactctcc   1140
caagtccatc aagagcggcg acgccgccat cgtcaggatg gagcccagca agcccatgtg   1200
cgtcgaggct ttcatcgagt acccgccgct cggccgcttc gccgtccgcg acatgaagca   1260
gaccattgcc gtcggcgtca tcaaggccgt cgagaagaag gaggctggcg gcaaggtcac   1320
caagagtgcg cagaaggccg ccgccaagaa gtga                              1354

<210> SEQ ID NO 2
<211> LENGTH: 450
<212> TYPE: PRT
<213> ORGANISM: Eimeria tenella

<400> SEQUENCE: 2

Met Gly Lys Glu Lys Thr His Ile Asn Leu Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Thr Ile Glu Lys Phe Glu Lys Glu Ser Ser Glu
        35                  40                  45

Met Gly Lys Ala Ser Phe Lys Tyr Ala Trp Val Leu Asp Lys Leu Lys
    50                  55                  60

Ala Glu Arg Glu Arg Gly Ile Thr Ile Asp Ile Ala Leu Trp Gln Phe
65                  70                  75                  80

Glu Thr Pro Ala Phe His Tyr Thr Val Ile Asp Ala Pro Gly His Arg
                85                  90                  95

Asp Phe Ile Lys Asn Met Ile Thr Gly Thr Ser Gln Ala Asp Val Ala
            100                 105                 110
```

```
Leu Leu Val Val Pro Ala Asp Gln Gly Gly Phe Glu Gly Ala Phe Ser
        115                 120                 125

Lys Glu Gly Gln Thr Arg Glu His Ala Leu Leu Ala Phe Thr Leu Gly
    130                 135                 140

Val Lys Gln Met Ile Val Gly Ile Asn Lys Met Asp Ala Thr Ser Pro
145                 150                 155                 160

Glu Lys Tyr Ser Glu Ala Arg Phe Asn Glu Ile Gln Ala Glu Val Ser
                165                 170                 175

Arg Tyr Leu Lys Thr Val Gly Tyr Asn Pro Glu Lys Val Pro Phe Val
            180                 185                 190

Pro Ile Ser Gly Phe Val Gly Asp Asn Met Val Glu Arg Ser Ser Asn
        195                 200                 205

Met Gly Trp Tyr Lys Gly Lys Thr Leu Val Glu Ala Leu Asp Ser Val
    210                 215                 220

Glu Pro Pro Lys Arg Pro Val Asp Lys Pro Leu Arg Leu Pro Leu Gln
225                 230                 235                 240

Asp Val Tyr Lys Ile Gly Gly Ile Gly Thr Val Pro Val Gly Arg Val
                245                 250                 255

Glu Thr Gly Val Leu Lys Pro Gly Met Val Val Thr Phe Ala Pro Ser
            260                 265                 270

Gly Leu Gln Thr Glu Val Lys Ser Val Glu Met His His Ala Gln Leu
        275                 280                 285

Glu Gln Ala Val Pro Gly Asp Asn Val Gly Phe Asn Val Lys Asn Val
    290                 295                 300

Ser Val Lys Asp Val Lys Arg Gly His Val Ala Ser Asp Ser Lys Asn
305                 310                 315                 320

Asp Pro Ala Lys Ala Ala Ala Ser Phe Gln Ala Gln Val Ile Val Leu
                325                 330                 335

His His Pro Gly Gln Ile Asn Pro Gly Tyr Thr Pro Val Leu Asp Cys
            340                 345                 350

His Thr Ala His Ile Ser Cys Lys Phe Ala Asp Leu Glu Lys Arg Leu
        355                 360                 365

Asp Arg Arg Ser Gly Lys Ala Leu Glu Asp Ser Pro Lys Ser Ile Lys
    370                 375                 380

Ser Gly Asp Ala Ala Ile Val Arg Met Glu Pro Ser Lys Pro Met Cys
385                 390                 395                 400

Val Glu Ala Phe Ile Glu Tyr Pro Pro Leu Gly Arg Phe Ala Val Arg
                405                 410                 415

Asp Met Lys Gln Thr Ile Ala Val Gly Val Ile Lys Ala Val Glu Lys
            420                 425                 430

Lys Glu Ala Gly Gly Lys Val Thr Lys Ser Ala Gln Lys Ala Ala Ala
        435                 440                 445

Lys Lys
    450

<210> SEQ ID NO 3
<211> LENGTH: 25
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 3
tgctggatcc atggggaagg aaaag                                    25
```

```
<210> SEQ ID NO 4
<211> LENGTH: 24
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 4
cacaaagctt gtcacttctt ggcg                                          24

<210> SEQ ID NO 5
<211> LENGTH: 27
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 5
gttcccgcgt ctgcccttcc ttggaga                                       27

<210> SEQ ID NO 6
<211> LENGTH: 27
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 6
tctccaagga agggcagacg cgggaac                                       27
```